United States Patent
Jarrell et al.

(10) Patent No.: US 6,560,922 B2
(45) Date of Patent: May 13, 2003

(54) METHOD OF PRODUCING VEGETABLE SPROUTS

(76) Inventors: Stephen Paul Jarrell, 485 Caldwell Cir., New Carlisle, OH (US) 45344; Richard Maurice Jarrell, 485 Caldwell Cir., New Carlisle, OH (US) 45344

( * ) Notice: Subject to any disclaimer, the term of this patent is extended or adjusted under 35 U.S.C. 154(b) by 41 days.

(21) Appl. No.: 09/861,513

(22) Filed: May 21, 2001

(65) Prior Publication Data

US 2001/0032415 A1 Oct. 25, 2001

Related U.S. Application Data

(63) Continuation-in-part of application No. 09/388,637, filed on Sep. 2, 1999.

(51) Int. Cl.[7] .................................................. A01G 00/25
(52) U.S. Cl. ............................................................. 47/58.1
(58) Field of Search .......................... 47/58.1, 14, 61, 47/15, 16, 66, 79, 80, 62

(56) References Cited

U.S. PATENT DOCUMENTS

| | | | |
|---|---|---|---|
| 4,180,941 A | * | 1/1980 | Korematsu ................. 47/14 |
| 4,551,942 A | * | 11/1985 | Brown ........................ 47/14 |
| 4,765,092 A | | 8/1988 | Cline |
| 4,941,282 A | | 7/1990 | Milstein |
| 5,205,068 A | | 4/1993 | Solomou |
| 5,636,474 A | * | 6/1997 | Lo ................................. 47/14 |
| 5,911,632 A | * | 6/1999 | Ko ............................. 111/199 |
| 5,934,011 A | * | 8/1999 | Ishioka et al. ................. 47/44 |
| 6,240,674 B1 | * | 6/2001 | Otake et al. .................. 47/56 |
| 6,256,926 B1 | * | 7/2001 | Nakada ........................ 47/61 |
| 6,357,176 B2 | * | 3/2002 | Baldwin et al. ............... 47/56 |
| 2001/0007687 A1 | * | 7/2001 | Wang .......................... 426/74 |

OTHER PUBLICATIONS

Meyerowitz, Sprouts the Miracle Food.
International Specialty Supply.
Malleshi Proximate Composition.
Reynolds, Drying Fruits & Vegetables.

* cited by examiner

Primary Examiner—Peter M. Poon
Assistant Examiner—Bethany L Griles
(74) Attorney, Agent, or Firm—Mark A. Navarre

(57) ABSTRACT

An improved and accelerated method of producing vegetable sprouts with surprisingly high levels of vitamin nutrients. In general, retention of high vitamin levels is improved by accelerating the growing cycle, and the growing cycle is accelerated by initially saturating the seed bed with a jet stream of water at a pressure in the range of 80–90 p.s.i. After the initial washing, the seeds are covered with a greenhouse dome, and placed under a light source. After an initial period, such as 12 hours, the seeds are periodically misted with water to complete the growth cycle. In experimental trials with broccoli, the sprouts were harvested after only 36 hours, and chemical analysis showed that the sprouts possessed surprisingly high levels of vitamin B-1, also known as thiamine.

5 Claims, 2 Drawing Sheets

METHOD OF PRODUCING VEGETABLE SPROUTS

RELATED APPLICATIONS

This application is a continuation-in-part of co-pending U.S. Patent application Ser. No. 09/388,637, filed Sep. 2, 1999.

TECHNICAL FIELD

This invention relates to a method of producing vegetable sprouts from seed, either for direct consumption or for dehydration and encapsulation as a dietary supplement.

BACKGROUND OF THE INVENTION

The beneficial attributes of vegetable sprouts as a dietary supplement are widely recognized, and several varieties of sprouts (bean, alfalfa, radish, broccoli, etc.) are commercially grown and marketed as a produce item in retail food outlets. Alternatively, the sprouts may be dehydrated, ground and encapsulated for consumption as a supplemental source of vitamins. Other health-related benefits, even including disease prevention, have also been claimed.

Methods utilized to sprout the vegetable seeds vary to some degree, but the recommended steps typically include: soaking the seeds in water for 12 hours or so, draining the seeds and placing them in a permeable but covered container, and periodically rinsing the seeds until ready for harvesting. Typically, the sprouts are harvested 3–5 days after being placed in the covered container. The ambient temperature can be controlled to encourage rapid growth, and lighting (either artificial or natural) may be used to encourage chlorophyll development. By way of example, see U.S. Pat. Nos. 4,765,092 and 4,941,282, and Meyerowitz's book, "The Complete Guide to Sprouting", published in 1998.

SUMMARY OF THE INVENTION

The present invention is directed to an improved and accelerated method of producing vegetable sprouts with surprisingly high levels of vitamin nutrients. In general, retention of high vitamin levels is improved by accelerating the growing cycle, and the growing cycle is accelerated by initially saturating the seed bed with high pressure water jet stream in the range of 80–90 pounds per square inch. Thereafter, the seeds are covered with a greenhouse dome, and placed under a light source. After an initial period, such as 12 hours, the seeds are periodically misted with water to complete the growth cycle. In experimental trials with broccoli, the sprouts were harvested after only 36 hours, and chemical analysis showed that the sprouts possessed surprisingly high levels of vitamin B-1, also known as thiamine.

DESCRIPTION OF THE PREFERRED EMBODIMENT

Figure 1:
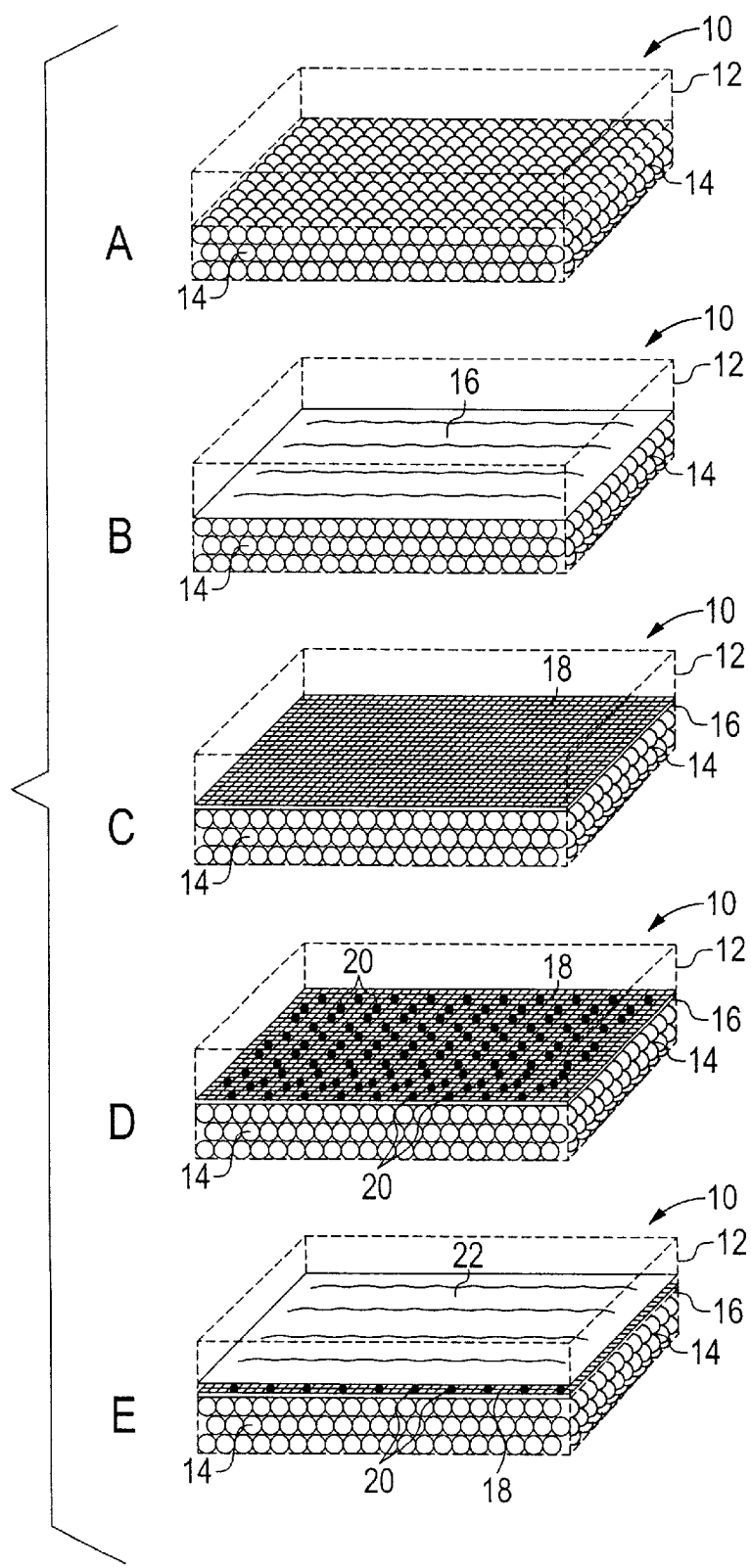
FIG. 1, parts A, B, C, D and E, depict a process for constructing a seed bed according to this invention.

In general, and referring to the drawings, the method of this invention is carried out by constructing a seed bed 10 in a shallow plastic tray 12 and then subjecting the seed bed 10 to a sequence of watering and lighting steps, after which mature sprouts are harvested. FIG. 1 illustrates the construction of the seed bed 10, while FIG. 2 illustrates the processing of the seed bed 10.

Referring particularly to FIG. 1, the letters A–E depict a portion of the seed bed 10, with the tray shown in outline, at various stages in the construction of the seed bed. The tray 12 is a conventional flat starter tray of any desired dimension, and is provided with bottom-side drain holes (not shown) to allow excess water to escape. First, as illustrated in portion A, a layer of perlite or similar inorganic beaded material 14 is placed in the bottom of the tray 12, to a depth of about ½ inch. This enables maximum absorption of air bubbles into the medium and acts as a buffer to absorb the high pressure water jet stream. Test results demonstrate that a medium grade perlite (approx. 3 mm×6 mm in cross-section) provide the fastest sprout growth and the highest nutrient levels in the sprouts. Second, as illustrated in portion B, the perlite material 14 is covered with a layer of paper towels 16. Third, as illustrated in portion C, a fine mesh nylon screen 18 is placed atop the paper towels 16. Fourth, as illustrated in portion D, the vegetable seeds 20 are spread evenly over the exposed surface of the screen 18. Finally, as illustrated in portion E, the seeds 20 are covered with a second layer of paper towels 22, completing the seed bed 10.

Figure 2:
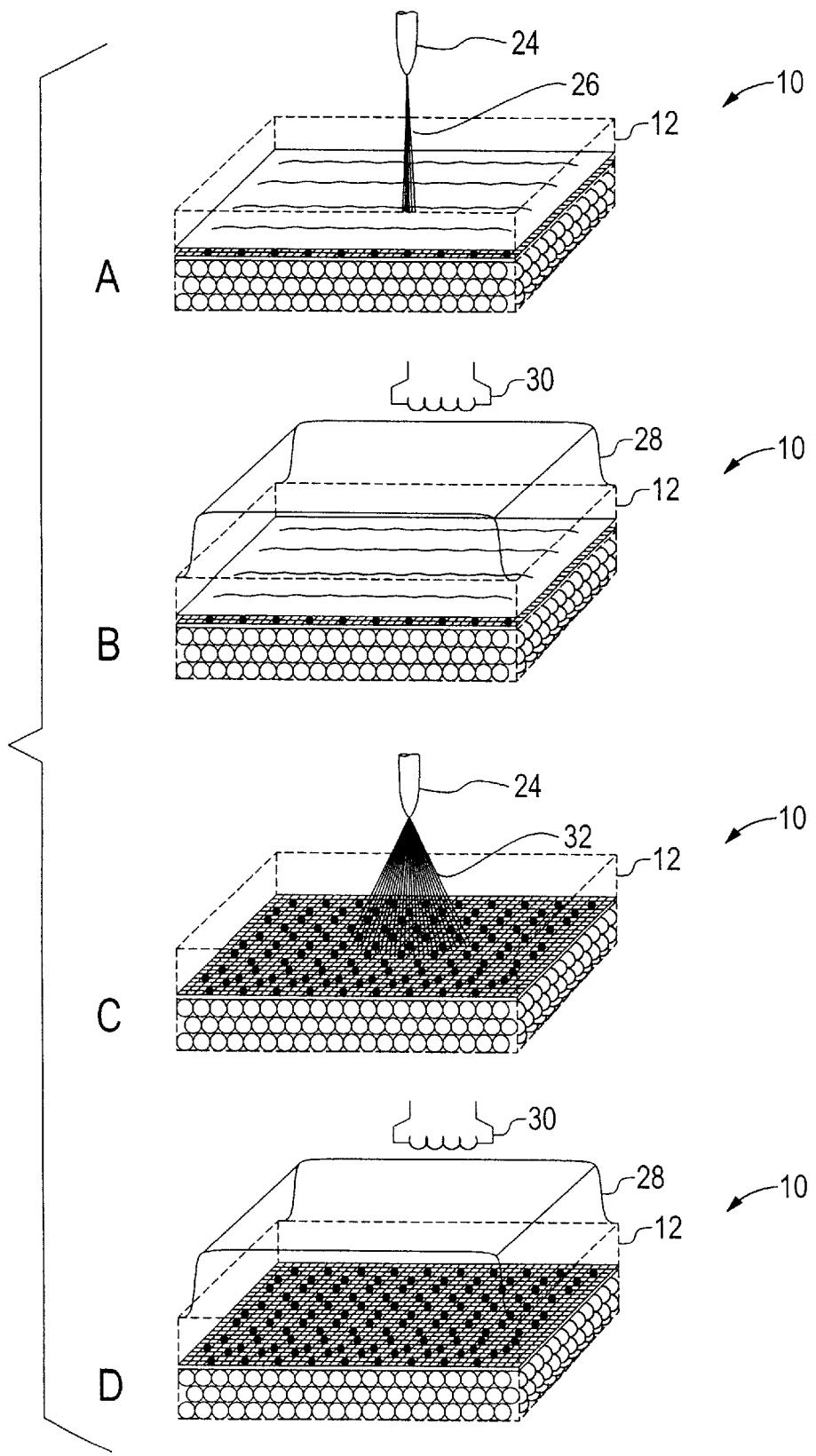
FIG. 2, parts A–D, depict a processing method for the seed bed of FIG. 1.

The processing of the seed bed 10 involves a number of steps, the major steps being illustrated by the portions A–D of FIG. 2. First, the seed bed 10 is misted with water to wet and settle the various layers in preparation for the high pressure jet spray. The high pressure jet spray, illustrated in portion A of FIG. 2, is carried out with a medium-duty all-purpose sprayer (such as those manufactured by Hudson Inc., for example) with an adjustable nozzle 24. Preferably, the sprayer tank is modified to accept a shrader tire valve and a pressure gauge, and the air in the tank is compressed to a pressure of 80–90 pounds per square inch (p.s.i.). The nozzle 24 is adjusted to deliver a narrow jet stream, as illustrated by reference numeral 26 in portion A of FIG. 2, which forces air bubbles into the medium grade perlite 14 and the area between the two paper towels 16, 22 where the seeds 20 are disposed. The jet stream 26 penetrates the towel layer 22 and saturates the underlying seeds 20 with a multitude of air bubbles, which is believed to be the stimulant that dramatically accelerates the germination process. Thus, the use of the high pressure jet stream 26 is believed to be a critical element of the present invention, with optimum results being achieved with a tank pressure in the range of 80–90 p.s.i. Pressures above this range tend to rip the paper towel 22, and appear to be unnecessarily high in any event. Pressures below this range result in decreased nutrient levels in the sprouts.

After the high pressure jet stream, the tray 12 is covered with a transparent greenhouse dome 28 and placed under a high intensity discharge (HID) lamp 30, as illustrated in portion B of FIG. 2. When a standard 11"×21" starter tray 12 is used, a single 400-Watt lamp 30 is sufficient, the lamp being spaced from the dome 28 by approximately three feet. After approximately twelve (12) hours, the dome 28 is removed, and the sprouting seeds 20 are separated from the upper towel layer 22 and evenly distributed on the screen 18. At this point, the spray nozzle 24 is adjusted to provide a low pressure water mist 32, and the seed bed 10 is thoroughly watered, as illustrated in portion C of FIG. 2. The dome 28 is then re-positioned on the tray 12 under the lamp 30, as illustrated in portion D of FIG. 2. The steps illustrated by portions C and D are repeated at 6-hour intervals until the sprouts are ready to harvest. If desired, the dome 28 may be removed three or so hours prior to harvest, and the seed bed 12 fanned lightly to slightly dry the sprouts and facilitate their removal from the screen 18. When the method of this invention is utilized with broccoli seeds, the sprouts are harvested approximately 24 hours after being separated from the upper towel layer 22.

Once harvested, the sprouts are preferably dried and encapsulated for ingestion as a vitamin supplement. The sprouts are preferably air-dried under a full spectrum lamp (simulating sunlight) such as the 400 Watt HID lamp 30 depicted in FIG. 2; with broccoli sprouts, this has been found to promote retention of sulforaphane. A conventional food processor or grinder may be used to finely grind the dried sprouts. Preferably, the ground sprouts are then re-dried prior to encapsulation.

In summary, this invention provides an accelerated method of producing vegetable sprouts with surprisingly high vitamin and nutrient levels. In the illustrated embodiment with broccoli seeds, the entire growing process requires only 36 hours, and the dried sprouts contained surprisingly high levels of vitamin B-1 and sulforaphane. The method may be practiced on a small or large scale, as desired, and the processing times and sequences may be adjusted somewhat to suit the particular circumstances. For example, it may be desired to use multiple lower-wattage lamps instead of the 400-Watt lamp 30, or it may be desired to provide ventilation for the sprouts in the final 24 hour growing period.

It is expected that various modifications in addition to those mentioned above will occur to those skilled in the art. Accordingly, it will be understood that methods incorporating the various mentioned and un-mentioned modifications may fall within the scope of this invention, which is defined by the appended claims.

What is claimed is:

1. A method of producing vegetable sprouts from vegetable seeds, comprising the steps of:

constructing a seed bed in a drained tray by: placing a layer of inorganic bead material in the tray, covering the bead material with a first towel layer, placing a screen on the first towel layer, distributing the vegetable seeds on the screen, and covering the vegetable seeds with a second towel layer;

processing the seed bed by: directing a jet stream of water in the range of 80–90 p.s.i. on the seed bed for stimulating the seeds and surrounding the seeds with air bubbles, covering the seed bed with a transparent dome and illuminating the seed bed with a high intensity lamp for an initial growth period during which the seeds grow sprouts, removing the second towel layer, and periodically watering the seed bed with a low pressure mist and illuminating the seed bed with the high intensity lamp for a final growth period during which the sprouts continue to grow; and harvesting the sprouts after the final growth period.

2. The method of claim 1, wherein the initial growth period is approximately twelve (12) hours.

3. The method of claim 1, wherein the final growth period is approximately twelve (12) hours.

4. The method of claim 1, wherein the step of processing the seed bed includes misting the seed bed with water prior to directing the jet stream of the seed bed.

5. The method of claim 1, including the step of drying the harvested sprouts with a full spectrum lamp.

* * * * *